US012698473B2

(12) United States Patent (10) Patent No.: US 12,698,473 B2
Kaga et al. (45) Date of Patent: Aug. 4, 2026

(54) CELL-CONTAINING STRUCTURE

(71) Applicants: Yuki Kaga, Yokohama (JP); Tomoaki Nakayama, Tokyo (JP); Tomoyuki Aratani, Yokohama (JP); Shinnosuke Koshizuka, Yamato (JP); Tatsuya Sameshima, Yokohama (JP); Momoko Shionoiri, Yokohama (JP); Tomofumi Kitazawa, Kawasaki (JP); Rie Ijichi, Tokyo (JP)

(72) Inventors: Yuki Kaga, Yokohama (JP); Tomoaki Nakayama, Tokyo (JP); Tomoyuki Aratani, Yokohama (JP); Shinnosuke Koshizuka, Yamato (JP); Tatsuya Sameshima, Yokohama (JP); Momoko Shionoiri, Yokohama (JP); Tomofumi Kitazawa, Kawasaki (JP); Rie Ijichi, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 982 days.

(21) Appl. No.: 17/935,846

(22) Filed: Sep. 27, 2022

(65) Prior Publication Data

US 2023/0105330 A1 Apr. 6, 2023

(30) Foreign Application Priority Data

Sep. 30, 2021 (JP) ................................. 2021-160843
Sep. 16, 2022 (JP) ................................. 2022-147770

(51) Int. Cl.
*C12N 5/0793* (2010.01)
(52) U.S. Cl.
CPC ........ *C12N 5/0619* (2013.01); *C12N 2503/02* (2013.01); *C12N 2506/45* (2013.01)
(58) Field of Classification Search
None
See application file for complete search history.

(56) References Cited

U.S. PATENT DOCUMENTS

| | | |
|---|---|---|
| 2016/0116459 A1 | 4/2016 | Mangan et al. |
| 2021/0277345 A1 | 9/2021 | Aratani et al. |
| 2021/0371816 A1 | 12/2021 | Nakayama et al. |

FOREIGN PATENT DOCUMENTS

| | | |
|---|---|---|
| JP | 6761409 | 9/2020 |
| JP | 2021-136998 | 9/2021 |
| JP | 2021-185780 | 12/2021 |
| WO | 2016/028880 | 2/2016 |
| WO | 2017/223052 | 12/2017 |

OTHER PUBLICATIONS

Extended European Search Report dated Feb. 21, 2023, in European Patent Application No. 22197578.2, 10 pages.
Odawara et al., "Toxicological evaluation of convulsant and anticonvulsant drugs in human induced pluripotent stem cell-derived cortical neuronal networks using an MEA system", Scientific Reports, vol. 8, 10416, 2018, pp. 1-11.
Russo et al., "Modeling the Interplay Between Neurons and Astrocytes in Autism using Human Induced Pluripotent Stem Cells", Biological Psychiatry, vol. 83, Apr. 1, 2018, pp. 569-578.
Sirenko et al., "Functional and Mechanistic Neurotoxicity Profiling Using Human iPSC-Derived Neural 3D Cultures", Toxicological Sciences, vol. 167, No. 1, 2019, pp. 58-76.
European Office Action dated Mar. 18, 2024, in European Application No. 22197578.2, 9 pages.
Frega et al., "Rapid Neuronal Differentiation of Induced Pluripotent Stem Cells for Measuring Network Activity on Micro-electrode Arrays", Journal of Visualized Experiments, vol. 119, Jan. 8, 2017, e54900, pp. 1-10. XP055965101.

*Primary Examiner* — Teresa E Knight
(74) *Attorney, Agent, or Firm* — Grüneberg Global IP, PLLC

(57) ABSTRACT

A cell-containing structure is provided that allows ready-to-use nerve drug response evaluation with high reproducibility to be easily performed. The cell-containing structure for evaluating an electrical property of neurons includes: (a) a culture surface to which the neurons are able to be adhered; (b) a cell mass that is adhered to the culture surface and contains at least one of the neurons; and (c) a plurality of electrodes for measuring the electrical property of the cell mass, wherein a spontaneous firing frequency of cells contained in the cell mass is 0.25 Hz or more per electrode.

15 Claims, 6 Drawing Sheets

CELL-CONTAINING STRUCTURE

CROSS-REFERENCE TO RELATED APPLICATIONS

This application claims the benefit of priority to Japanese Application No. 2021-160843, filed on Sep. 30, 2021, and Japanese Application No. 2022-147770, filed on Sep. 16, 2022. The content of each of these applications is hereby incorporated by reference in its entirety.

BACKGROUND OF THE INVENTION

Field of the Invention

The present invention relates to a cell-containing structure.

Description of Related Art

Drug development for the central nervous system has been mainly conducted in experiments with model animals and their cells, but due to species specificity of the neural response, it is well known in the pharmaceutical industry that human-specific actions have not been able to be detected in the preclinical stage so far. Here, in recent years, as one in vitro pharmacological and toxicity evaluation test method, constructing a cell evaluation system using human-derived induced pluripotent stem cells (hiPSC), has been expected. It is already known that, if human-specific side effects can be detected by neurological evaluation in a preclinical-stage in vitro test, it is possible to eliminate detection of side effects in the clinical stage, and it is possible to avoid returning from the clinical stage to the preclinical stage, which leads to a significant reduction in the cost of new drug development.

Here, an action potential of neurons may be used to evaluate the efficacy and toxicity of neurons. As one method of detecting and evaluating an action potential of neurons, an evaluation method using a microelectrode array (MEA) is known. The MEA is an array of microelectrodes arranged on a substrate for cell culture and can detect electrical activity of cells, It is known that, when neurons derived from hiPSCs are cultured on an MEA and the action potential is detected, it is necessary to culture neurons at a higher density and for a longer time than when non-human animal-derived neurons are used. In addition, when iPSC-derived cells are handled in their own laboratory, know-how is required and high costs are incurred for cell maintenance and differentiation, and thus there is a demand for ready-to-use plates that can be purchased as assay plates on which cells are seeded.

SUMMARY OF THE INVENTION

An object of the present invention is to obtain a cell-containing device that allows evaluating drug responses to neurons to be easily performed with ready-to-use and high reproducibility.

In nerve drug response evaluation using neurons derived from human induced pluripotent stem cell (hiPSC-Neuron) in the related art, after a user selects and acquires a substrate on which to place cells, the cells are processed and cultured, a neural network is constructed on the substrate, and thus it is necessary to investigate the effects of various test compounds on the nerves. In this case, since it takes time to complete evaluation, and the morphology and function of cells as well as the composition and culture conditions of cells during evaluation differ for each user, there is a high barrier to evaluating drug responses to neurons having high reproducibility using hiPSC-Neuron.

For example, in order to construct a clinically meaningful cell model with an improved hiPSC-Neuron cultured product that can show synchronous bursts of neural networks in vitro, Patent Document 1 (Japanese Patent No. 6761409) discloses a neuron cultured product in which exciting neurons and inhibitory neurons are co-cultured in various ratios, and astrocytes are additionally added to the culture as necessary, and a method of preparing the same. However, the evaluation results are not stable because there are no clear criteria indicating that neurotoxicity evaluation is possible regarding the state of the cultured product. The inventors found new problems in that since no certain criteria are set for properties and states of cell masses used in the conventional assay during development of a ready-to-use cell culture tool, it is difficult to perform direct comparison of the obtained data, and it is difficult to obtain stable and highly reproducible data from the results themselves.

A cell-containing structure according to the present invention is a cell-containing structure for evaluating an electrical property of neuro s, including (a) a culture surface to which the neurons are able to be adhered; (b) a cell mass that is adhered to the culture surface and contains at least one of the neurons; and (c) a plurality of electrodes for measuring the electrical property of the cell mass, wherein a spontaneous firing frequency of cells contained in the cell mass is 0.25 Hz or more per electrode.

The present invention can provide a cell-containing structure that allows ready-to-use nerve drug response evaluation with high reproducibility to be easily performed.

DETAILED DESCRIPTION OF THE INVENTION

[Cell-Containing Structure]

Figure 1:
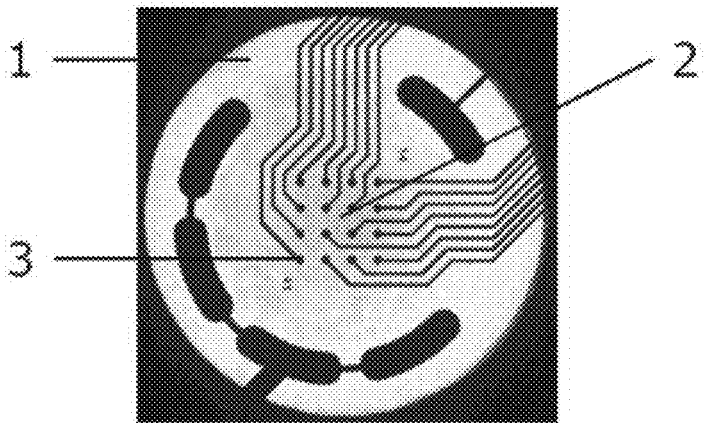
FIG. 1 is a photo image showing a photographic image of a well of a plate of this example obtained using a microscope.

In one embodiment, the present invention provides a cell-containing structure for evaluating an electrical property of neurons, including:

(a) a culture surface to which the neurons are able to be adhered;

(b) a cell mass that is adhered to the culture surface and contains at least one of the neurons: and (c) a plurality of electrodes for measuring the electrical property of the cell mass, wherein a spontaneous firing frequency of cells contained in the cell mass is 0.25 Hz or more per electrode As will be described below in examples, the inventors have found a cell-containing structure having the following features in evaluating electrophysiological drug responses to neurons using various neurons, for example, hiPSC-Neuron. Criteria are set for the state of cultured products composed of cell masses containing hiPSC-Neuron, which can be used for electrophysiological neurotoxicity evaluation with favorable reproducibility, and a cultured product that satisfies the criteria is adhered to a substrate used for evaluation. In short, common electrophysiological properties of the cultured product when the effects of the cultured product exposed to a plurality of test compounds having different mechanisms in evaluating nerve functions are stably obtained in all the test compounds are extracted. In addition, these are used as the criteria for the state of the cultured product that can be used for evaluating electrophysiological drug responses to neurons with favorable reproducibility, and a cultured product that satisfies the criteria is adhered to a substrate used for evaluation.

When a cell-containing structure containing a cultured product that satisfies certain criteria and a substrate such as a cell-containing container is used, it is possible to perform evaluating electrophysiological drug responses to neurons without each user selecting, acquiring, or processing a substrate on which to place cells, and using a conditional operation after culturing. Therefore, it does not take time to complete evaluation and certain criteria are set for the morphology and function of cells during evaluation, and thus it is possible to perform evaluating drug responses to neurons with high reproducibility. Therefore, when the cell-containing structure of the present embodiment is used, it is possible to easily perform ready-to-use evaluating drug responses to neurons with high reproducibility.

The cell-containing structure includes cells and a structure containing (for example, holding and storing) the cells. The structure broadly includes a container (cell-containing container) in which cells are cultured on the structure, a plate to which cells are adhered and the like, as will be described below

[Neurons]

In one embodiment of the present invention, neurons are used as the cells. The neurons are preferably cells differentiated in vitro. As the neurons differentiated in vitro, for example, cells obtained by differentiating pluripotent stem cells into neurons in vitro can be used. In addition, it is also possible to use cells that have been dedifferentiated temporarily and then redifferentiated.

Examples of pluripotent stem cells include embryonic stem cells (ES cells) and induced pluripotent stem cells. Examples of induced pluripotent stem cells include nuclear transfer embryonic stem cells (ntES cells) and induced pluripotent stem cells (iPSCs). Among these, iPSCs are preferable as pluripotent stem cells.

iPSCs may be derived from healthy people or may be derived from patients having various nervous diseases (nervous system diseases). In addition, the cells may be cells that have been subjected to various types of gene editing, and may be, for example, cells that have been engineered to have genes that are causes or risk factors of various nervous diseases according to gene editing.

When iPS cells are cells derived from patients having various nervous diseases, they can be used to construct a disease model for the nervous system. Nervous diseases are not particularly limited, and examples thereof include neurodegenerative diseases, autism, epilepsy, attention-deficit hyperactivity disorder (ADHD), schizophrenia, and bipolar disorder. Examples of neurodegenerative diseases include Alzheimer's disease, Parkinson's disease, and amyotrophic lateral sclerosis (ALS).

Among these nervous diseases, use can particularly be for autism, epilepsy, schizophrenia, ADHD, ALS and bipolar disorder disease.

The animal species from which neurons are derived are not particularly limited, and examples thereof include humans, monkeys, dogs, cows, horses, sheep, pigs, rabbits, mice, rats, guinea pigs, and hamsters. Among these, humans are preferable. That is, neurons are particularly preferably neurons derived from human induced pluripotent stem cells (hiPSC).

In addition, neurons may be of a single type or a mixture of two or more types of neurons. Neurons can be roughly classified into, for example, peripheral nerves and central nerves. Examples of peripheral nerves include sensory neurons, motor neurons, and autonomic neurons. Examples of central nerves include intervening neurons and projection neurons. Examples of projection neurons include cortical neurons, hippocampal neurons, and amygdala neurons. In addition, central neurons can be roughly classified into excitatory neurons and inhibitory neurons. Glutamic acid-operated neurons mainly responsible for excitatory transmission in the central nervous system and γ-aminobutyric acid (GABA)-ergic neurons mainly responsible for inhibitory transmission may be exemplified.

Other neurons that release neuromodulators include cholinergic neurons, dopaminergic neurons, noradrenergic neurons, serotonergic neurons, histaminergic neurons and the like.

In addition, specific examples of cells used for obtaining neurons obtained by differentiation as above in vitro include cells of Quick-Neuron (TM) series (commercially available Elixirgen Scientific). These cells are pluripotent stem cells that have been induced to differentiate into neurons and differentiate into functionally tnature neurons in about 10 days.

In addition, depending on purpose, mature neurons are preferable, and for example, neurons in which the expression of any of marker genes of Tubulin beta3, MAP2, NeuN, 160 kDa Neurofilament, 200 kDa Neurofilament, NSF, PSD93, and PSD95 is positive are preferable.

[Culture Surface]

A cell-containing structure of one embodiment has a culture surface to which the neurons can adhere. The culture surface is provided on one surface of the cell-containing structure. In one embodiment of the present invention, the cell-containing structure is a cell culture container, and the culture surface is provided on one surface in the cell culture container.

The cell culture container is a container in which cells are accommodated and cells are cultured in the container. The cell culture container may be a container generally used for cell culture, and examples thereof include a dish and a well plate. The diameter of the dish, the number of wells of the well plate, and the like can be appropriately selected depending on applications. As will be described below, an electrode array is arranged on the culture surface of the cell culture container as a plurality of electrodes for measuring an electrical property. That is, the cell-containing container obtained by the production method of the present embodiment is a microelectrode array (MEA) plate. The nutriber of electrodes of the MEA and the like can be appropriately selected depending on applications.

Examples of materials of the culture surface of the cell culture container include organic materials and inorganic materials described below. These may be used alone or two or more thereof may be used in combination.

The organic material is not particularly limited, and can be appropriately selected depending on purposes, and examples thereof include acrylic materials such as polyethylene terephthalate (PET), polystyrene (PS), polycarbonate (PC), triacetyl cellulose (TAC), polyimide (PI), nylon (Ny), low-density polyethylene (LDPE), medium-density polyethylene (MDPE), vinyl chloride, vinylidene chloride, polyphenylene sulfide, polyether sulfone, polyethylene naphthalate, polypropylene, and urethane acrylate, silicone materials such as cellulose and polydimethylsiloxane (PDMS), polyvinyl alcohol (PVA), alginate metal salts such as calcium alginate, and gel-like materials such as polyacrylamide, methylcellulose, and agarose.

The inorganic material is not particularly limited, and can be appropriately selected depending on purposes, and examples thereof include glass and ceramics.

The culture surface of the cell culture container may be coated with a coating agent. As the coating agent, those generally used for cell culture can be appropriately used, and examples thereof include collagen, Matrigel (registered trademark, commercially available from Corning Inc.), Geltrex (commercially available from Thermo Fisher Scientific), PLO (commercially available from Sigma-Aldrich Co. LLC), PDLO (commercially available from Sigma-Aldrich Co. LLC), fibronectin, fibrinogen, gelatin, polyethyleneimine (PEI), and laminin, In particular, it is preferable that a substrate which is an extracellular matrix be present on the surface of the cell culture. When a substrate which is an extracellular matrix is provided, cells easily adhere to the culture surface, and it is possible to inhibit separation of the cells. As the substrate which is an extracellular matrix, a substance known in the related art as an extracellular matrix may be used, and examples thereof include collagen, fibrinogen and laminin among the above coating substances, and laminin is particularly preferably used.

Figure 2:
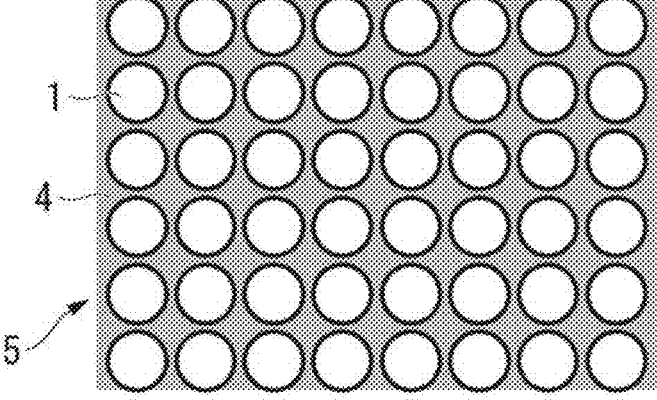
FIG. 2 is a schematic view showing arrangement of wells of the plate of this example.

The cell culture container is preferably a plate in which wells (recesses and grooves) as a container are provided. As shown in FIG. 2 to be described below, the plate is preferably a well plate in which cylindrical wells are arranged. In one embodiment, as shown in FIG. 2, a 48-well type is preferably used in terms of measurement scale such as the type of the measurement compound and the number of trials. The number of wells may be appropriately changed depending on the type of the test compound to be tested at one time and the number of trials, and for example, a standardized well plate having a plurality of wells such as 6, 24, 48, 96, 384, and 1536 may be used.

For adhesion of the neurons, adhesion by culturing neurons on the culture surfaces is preferable. As the medium used for culture, a meditun in which necessary components are added to a basal medium can be used. Examples of basal mediums include BrianPhys (,commercially available from STEMCELL Technologies), Neurobasal (commercially available from Thermo Fisher Scientific), Dulbecco's Modified Eagle's Medium (DMEM), Ham's F12 medium (Ham's Nutrient Mixture F12), D-MEM/F12 medium, McCoy's 5A medium, Eagle's MEM medium (Eagle's Minimum Essential Medium, EMEM), α MEM medium (alpha Modified Eagle's Minimum Essential Medium, αMEM), MEM medium (Minimum Essential Medium), RPM I1640 (Roswell Park Memorial Institute-1640) medium, Iscove's Modified Dulbecco's Medium (IMDM), MCDB131 medium, William's medium E, IPL41 medium, Fischer's medium, M199 medium, high performance improved 199 medium (High Performance Medium 199), StemPro34 (commercially available from Thermo Fisher Scientific), X-VIVO 10 (commercially available from Chembrex), X-VIVO 15 (commercially available from Chembrex), HPGM (commercially available from Chembrex), StemSpan H3000 (commercially available from STEMCELL Technologies), StemSpanSFEM (commercially available from STEMCELL Technologies), Stem (commercially available from Sigma-Aldrich Co. LLC). QBSF-60 (commercially available from Quality Biological), Stem ProhESCSFM (commercially available from Thermo Fisher Scientific), Essential 8 (registered trademark) medium (commercially available from Thermo Fisher Scientific), mTeSR1 or mTeSR2 medium (commercially available from STEMCELL Technologies), ReproFF or ReproFF2 (commercially available from Reprocell Inc.), PSGro hESC/iPSC medium (commercially available from System Biosciences), NutriStem (registered trademark) medium (commercially available from Biological Industries), CSTI-7 medium (commercially available from Cell Science & Technology Institute, Inc.), MesenPRO RS medium (commercially available from Thermo Fisher Scientific), MF-Medium (registered trademark) mesenchymal stein cell growth medium (commercially available from Toyobo Co., Ltd.), Sf-900II (commercially available from Thermo Fisher Scientific), and Opti-Pro (commercially available from Thermo Fisher Scientific). These may be used alone or two or more thereof may be used in combination.

In addition, examples of additives added to basal mediums include those generally used for culturing neurons, and examples thereof include SM1 supplement (commercially available from STEMCELL Technologies), N2 supplement A (commercially available from STEMCELL Technologies), rat astrocyte culture supernatant (commercially available from FUJIFILM Wako Pure Chemical Corporation), human astrocyte culture supernatant (commercially available from ScienCell Research Laboratories), Component N (commercially available from Elixirgen Scientific), Component G2 (commercially available from Elixirgen Scientific), Component P (commercially available from Elixirgen Scientific), N2 Supplement (commercially available from Thermo Fisher Scientific), Well Neural Supplement B (commercially available from CDI), iCell Nervous System Supplement, and B-27 plus (commercially available from Thermo Fisher Scientific).

[Cell Mass]

The cell mass adheres to the culture surface, and contains at least one of the neurons.

The cell mass may further contain astrocytes.

The astrocytes may be primary cultured cells or astrocytes that have been induced to differentiate from pluripotent stem cells. Examples of pluripotent stem cells include the same ones described above. As the astrocytes, for example, one derived from a human fetus can be used.

In the process in which pluripotent stem cells that had been induced to differentiate into neurons and astrocytes are mixed, and seeded in a cell culture container in which an electrode array is arranged on a culture surface, the ratio of the pluripotent stem cells and astrocytes to be mixed (the number of pluripotent stem cells:the number of astrocytes) is preferably 1:1 to 4:1. When pluripotent stem cells and astrocytes are mixed at a ratio within the above range, the differentiated neurons maintain an aggregation level at which the action potential can be detected, and the action potential can be detected well.

In addition, a total cell number of the pluripotent stem cells and the astrocytes per unit area of the culture surface of the cell culture container is preferably 2,500 to 300,000 cells/cm$^2$, for example, 2,800 to 300,000 cells/cm$^2$.

The period for which pluripotent stem cells and astrocytes are mixed and seeded and the cell culture container is then incubated can be appropriately set depending on purposes, and is preferably a time sufficient for at least pluripotent stem cells to differentiate into neurons. For example, when cells of Quick-Neuron (TM) series (commercially available from Elixirgen Scientific) are used, the period is at least about 10 days after cell seeding.

For example, when the action potential is detected in neurons that have been induced to differentiate from human iPS cells, the period can be, for example, 30 days or longer, for example, 40 days or longer, for example, 50 days or longer, for example, 60 days or longer, or for example, 70 days or longer, from when pluripotent stem cells and astrocytes are mixed and seeded.

When pluripotent stem cells that have been induced to differentiate into neurons, and astrocytes are mixed and seeded, it is possible to inhibit separation of the neurons from a culture surface of a cell culture container (MEA plate) in which an electrode array is arranged. In addition, when pluripotent stem cells before differentiation that have been induced to differentiate into neurons are seeded instead of differentiated neurons, it is possible to further inhibit separation of neurons.

The cell-containing container of the present embodiment may further contain oligodendrocytes, microglia and the like as well as neurons and astrocytes. For example, when the cell mass contains oligodendrocytes andlor microglia, an environment similar to the human brain can be obtained. Specifically, oligodendrocytes are thought to form the spinal cord and accelerate conduction of neurons.

The adhesion area of these cells to the culture surface of the culture container is 0.5 mm$^2$ or more, preferably 0.949 mm$^2$ or more, more preferably 3 mm$^2$ or more, and still more preferably 3.14 mm$^2$ or more per 80,000 total cells. In addition, the upper limit of the adhesion area of cells to the culture surface of the culture container is preferably about 28.2 mm$^2$.

In this specification, the adhesion area of the cells to the culture surface of the culture container is an area on the culture surface of a region in which an aggregation of regions (cell bodies) in which nuclei are present adhere to the culture surface among cells including neurons and astrocytes. That is, the area of the region in which only protrusions (dendrites and axons) of neurons and protrusions of astrocytes adhere to the culture surface of the culture container is not included in the above adhesion area.

For adhesion between the cell-containing structure and the cell mass, for example, the cells may be held in the cell-containing container or the cells may be cultured on the cell-containing container. In particular, it is preferable that cells be cultured on the cell-containing container and the cell mass be adhered to the culture surface.

[Electrical Property]

The cell-containing structure of one embodiment of the present invention is a structure for evaluating an electrical property of the neurons. The electrical property of a neurons is an action of the electrical activity of the cell and particularly, the action potential of the neurons. In addition, it particularly refers to a change in the action potential associated with a particular stimulus, and particularly a response of the neurons to a test compound such as a drug.

The cell-containing structure includes a plurality of electrodes for measuring the electrical property. Specifically, a cell culture structure in which an electrode array is arranged on the culture surface is preferable. As such a structure, the above MEA plate as a plate constituting a cell-containing container may be exemplified.

In the cell-containing structure, the spontaneous firing frequency of the cells contained in the cell mass is 0.25 Hz or more per electrode. The spontaneous firing frequency means the number of extracellular potential fluctuations derived from individual cell spikes detected per unit time. For the spontaneous firing frequency, for example, a total number of detected extracellular potential fluctuations (a total number of electrical signals measured in one multi-point electrode array) of electrical signals emitted from the neurons contained in the cultured product adhered to the substrate, which are detected by one or more electrodes at the bottom of the well of the substrate, is divided by the measurement time and the number of electrodes, and thus the spontaneous firing frequency per electrode can be calculated. In addition, the spontaneous firing frequency here is not a measurement of synchronous firing (also referred to as synchronous burst, network burst or the like) of the entire cell mass but a measurement of spontaneous firing of individual cells per electrode.

According to a cell-containing structure with a criterion in which the spontaneous firing frequency of the cells contained in the cell mass is 0.25 Hz or more per electrode, it is possible to reduce a variation in the reaction rate of the firing frequency after exposure to a test compound when an electrical property is measured.

In the cell-containing structure, when the spontaneous firing frequency in the cell mass is less than 0.25 Hz per electrode, the results may vary greatly even if the electrical property is measured under the same condition. The upper limit of the spontaneous firing frequency is not particularly set, and it varies depending on the measurement device and conditions used, but, as a guide, for example, in the case of the extracellular measurement device to be described below, it is preferably less than 31.25 Hz.

The above determination in which the spontaneous firing frequency of the cells contained in the cell mass is 0.25 Hz or more per electrode can be performed by producing the cell-containing structure by a conventionally known method, and then detecting the spontaneous firing frequency per electrode for the cell-containing structure. Specifically, the spontaneous firing frequency can be detected by acquiring, for example, extracellular potential data. A raster plot of extracellular potential data is acquired using the extracellular measurement device. Then, the raster plot is analyzed to obtain the number of peaks (the number of spikes) per hour.

The spontaneous firing frequency (Hz) can be detected from the number of spikes per hour.

Here, according to the above one embodiment, when a cell-containing structure in which a cell mass is adhered to a cell culture container is produced, a sufficient cell-containing structure in which the spontaneous firing frequency in the cell mass measured by the above measurement method is 0.25 Hz per electrode can be obtained.

The electrical property is preferably detected by a response to at least one stimulus treatment applied to the cells or cell mass. Such a stimulus treatment includes some operations of applying a stimulus to cells and may be a physical or chemical stimulus. Examples of physical treatments include vibration and a change in pressure of a gas or the like under culture conditions. Examples of chemical treatments include addition of a compound, a change in the gas component in a culture environment, and a change in the gas concentration, for example, a change in the $CO_2$ concentration.

The stimulus treatment is preferably exposure to at least one test compound. The test compound may be a physiologically active substance such as various drugs.

The test compound is preferably an agonist or antagonist of a neurotransmitter receptor. When the electrical property of neurons with respect to an agonist or antagonist of a neurotransmitter receptor is examined, it can be suitably used for screening drugs related to neurotransmission The test compound is preferably an ion channel blocker. When the electrical property of neurons with respect to the ion channel blocker is examined, it can be suitably used to obtain information on the action of blocking an ion stimulus.

For the test compound used for evaluating neurotoxicity, as a compound that competes with the binding of neurotransmitters to receptors related to neurotransmission, Pilocarpine, Phenytoin, Zonisamide or the like is preferable. In addition, picrotoxin, gabazine, D-AP5, CNQX, Strychnine or Pentylenetetrazole can be used. As the ion channel blocker (ion channel inhibitor), 4-AP, carbamazepine or the like can be used.

EXAMPLES

Next, the present invention will be described in more detail with reference to examples, but the present invention is not limited to the following examples.

Experimental Example 1

(Preparation of MEA Plate)

A multi-electrode array (MEA) plate was prepared as a cell-containing container which is a cell-containing structure of the present embodiment.

As a plate used for the MEA plate, CytoView MEA Plate (commercially available from Axion Biosystems) having 6×8 wells (a total of 48 wells) and a micro electrode array on the well bottom was used.

For the plate, first, as a pretreatment, 70% ethanol was added to the wells, and the plate was left at room temperature for 5 minute. Then, the ethanol in the wells was aspirated and dried in air, A D-MEM/F12 medium containing antibiotics and bovine-derived serum was added to the wells and left at room temperature for 2 minutes. The medium in the wells was aspirated and distilled water was then added to the wells. Distilled water in the wells was aspirated and dried in air.

Then, the plate was coated. After a 50% poly(ethylene-imine) solution (PEI, Sigma-Aldrich) was adjusted with a boric acid solution diluted to 2.5 mMwithdistilled water so that the final concentration was 0.1%, 50 μl thereof was added to each of the wells, and the mixture was left at 37° C. for 1 hour. After 0.1% PEI in the wells was aspirated, the wells were washed with distilled water 5 times and dried in air.

After that, 50 μl of 30 μg/ml Matrigel (CORNING) was added to each well and left to stand at 37° C. for 1 hour. After aspirating 30 μg/ml Matrigel in the wells, each well was washed once with distilled water and air-dried.

Then, the cells were seeded on the plate. For thawing and preparation of cells, a medium A containing the following was prepared.

Meditun A: D-MEM/F12 medium, Neurobasal™ Medium (Thermo Fisher SCIENTIFIC), Gibco™ Glutamax™ Supplement (Thermo Fisher SCIENTIFIC), Component N (Elixirgen Scientific), Component G2 (Elixirgen Scientific), Component P (Elixirgen Scientific), Penicillin-Streptomycin, Y-27632 2HCl (Selleck)

According to the instruction manual, hiPSC-Neuron derived from healthy people and astrocytes derived from a human fetus were thawed, and suspended in the medium A. In order to prevent the cell mass and its cultured product from being separated from the substrate, laminin (commercially available from Thermo Fisher Scientific) was added to the cell suspension so that the final concentration was 20 μg/ml. In addition, the cell suspension contained either or both of microglial cells and oligodendrocytes.

As a cell seeding operation, 10 μl of each cell suspension was dispensed into micro electrode parts of the wells, and left in a cell incubator at a temperature of 37° C. and a $CO_2$ concentration of 5% for 1 hour. 300 μl of the medium A was added to the wells in which the cell suspension was dispensed. 5 ml of DPBS was added around the wells of the MEA plate. The sample was left in a cell incubator at a temperature of 37° C. and a $CO_2$ concentration of 5% for 1 day.

Here, FIG. 1 shows an enlarged view of one well unit arranged on the plate, and FIG. 2 shows a schematic view of a well plate in which wells are arranged on a plate 4. FIG. 1 is a photographic image of a well obtained using a microscope, and a cultured product 2 composed of cell masses containing hiPSC-Neuron and astrocytes derived from a hwnan fetus is adhered to a well bottom 1 (culture surface).

In the main test, the action potential of neurons adhered onto a micro electrode 3 arranged on the well bottom as shown in FIG. 1 was measured as an extracellular potential, and the neurotoxicity was evaluated from the change in extracellular potential when the test compound was treated.

Cell culture and periodic inspection were performed as follows. The medium in the well was aspirated, the medium A containing no Y-27632 2HCl was dispensed into the wells so that the amount thereof was 300 μl per well, and left in a cell incubator at a temperature of 37° C. and a $CO_2$ concentration of 5% for 2 days. The medium was aspirated so that the amount ofthe medium in the well was 150 μl per well, 150 μl of the new medium A containing no Y-27632 2HCl was added and the mixture was then left in a cell incubator at a temperature of 37° C. and a $CO_2$ concentration of 5% tier 4 days.

Next, a medium B containing the following was prepared. Medium B: Neurobasal Plus Medium (Thermo Fisher SCIENTIFIC), B-27™ Plus Supplement (Thermo Fisher SCIENTIFIC), Gibco™ Glutamax™ Supplement (Thermo Fisher SCIENTIFIC), ascorbic acid filtered with a 0.22 μm filter after the concentration was adjusted to 200 mM with distilled water, Penicillin-Streptomycin, medium for neurons (commercially available from FUJIFILM Wako Pure Chemical Corporation).

The medium was aspirated so that the amount of the medium in the well was 150 μl per well, 150 μl of the medium B was added and the mixture was then left in a cell incubator at a temperature of 37° C. and a $CO_2$ concentration of 5% for 3 days. After 3 days, the medium was aspirated so that the amount was 150 μl per well, the medium B was added, the mixture was then left, and this process was repeated until the time of shipping.

[Extracellular Potential Data]

From 22 days after cell seeding, once a week, extracellular potential data was acquired for 10 minutes using an extracellular measurement device maestro (Axion Biosystems).

Figure 3:
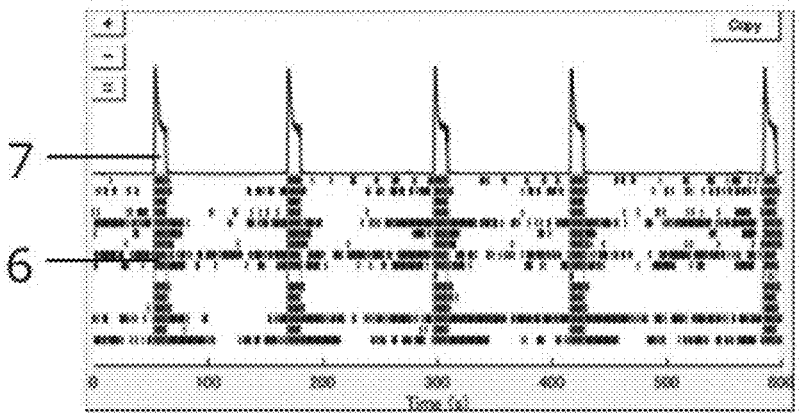
FIG. 3 is a graph showing a raster plot of extracellular potential data of this example and the number of detected spikes.

FIG. 3 shows a graph of a raster plot of extracellular potential data and the number of detected spikes. That is, using maestro Pro (commercially available from Axion Biosystems), for the prepared MEA Cytoview Plate (commercially available from Axion Biosystems), the results of the extracellular potential of the cultured product 2 composed of cell masses containing hiPSC-Neuron and astrocytes derived from a human fetus, which were adhered to the well bottom 1 shown in FIG. 1 and FIG. 2, measured using maestro Pro for 10 minutes are illustrated as a raster plot 6 of FIG. 3 and a graph 7 of the number of detected spikes. That is, the raster plot shows the potential change (spontaneous fire) of each cell, and the peaks in the graph 7 can be drawn with the number of spikes in the raster plot 6 as the height of the line. The spontaneous firing frequency (Hz) can be detected from the number of peaks in the graph 7 per hour.

In wells without laminin suspension or matrigel coating, cell detachment occurred prior to the time point at which spontaneous firing was detected and no spontaneous firing could be detected.

Figure 4:
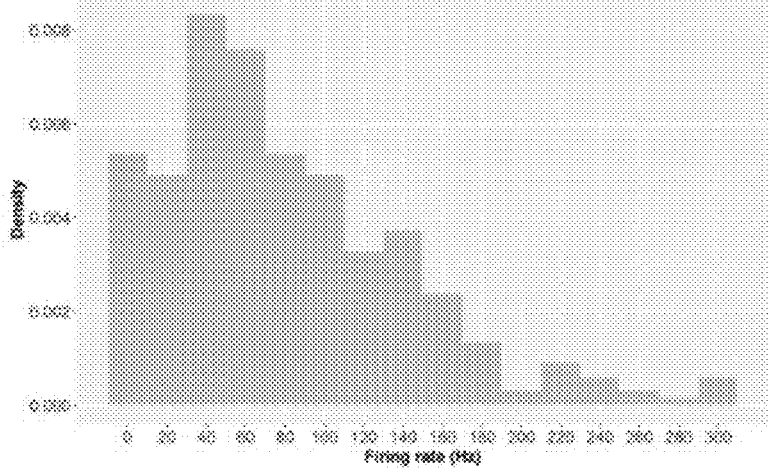
FIG. 4 is a graph showing a frequency distribution diagram of spontaneous firing frequencies for each well obtained from the measurement data of this example.

FIG. 4 shows a frequency distribution diagram of the spontaneous firing frequency for each well obtained from the measurement data. It was confirmed that the spontaneous firing frequency was 4 Hz or more using the extracellular potential measurement data obtained in the above method. In the MEA plate used in this example, since the number of electrodes per well was 16, it was confirmed that the spontaneous firing frequency was 4 Hz/16=0.25 Hz or more per electrode.

Figure 9:
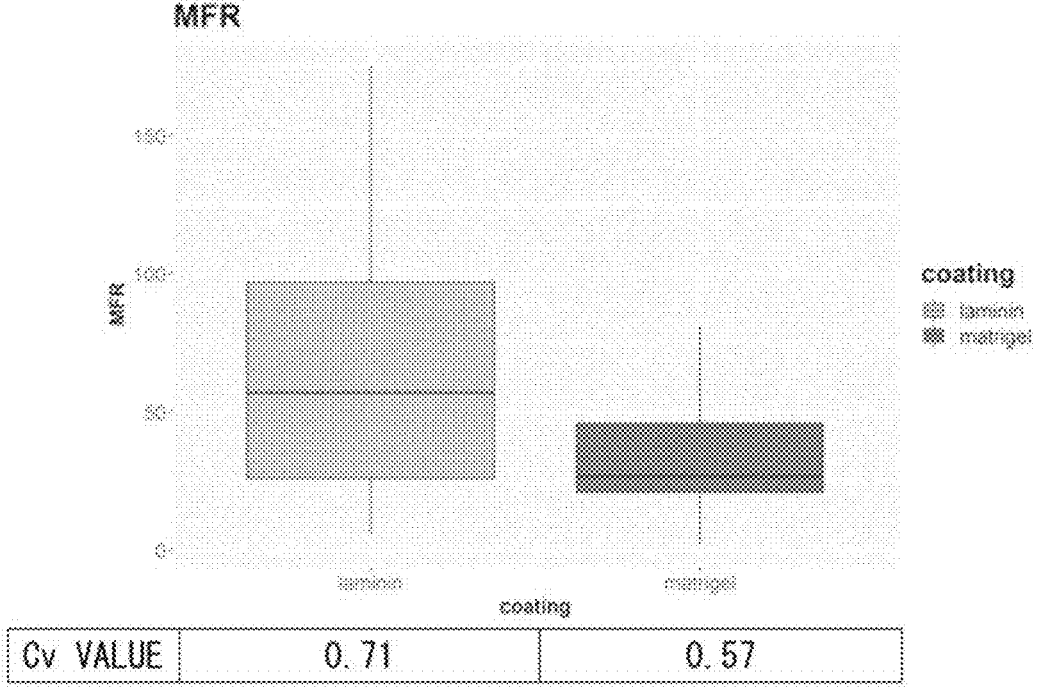
FIG. 9 is a graph showing a comparison of spontaneous firing frequencies between laminin suspension and matrigel coating.

Further, FIG. 9 also shows the spontaneous firing frequency per 16 electrodes when the coating conditions were laminin suspension and matrigel coating. The Cv value, which indicates variation between wells, was 0.71 when laminin was suspended and 0.57 when tnatrigel-coated. Therefore, it was confirmed that Matrigel coating reduced the amount by about 20% compared to the laminin suspension, indicating that variation between wells was suppressed.

[Evaluation of Electrophysiological Neurotoxicity of Test Compound]

Figure 5:
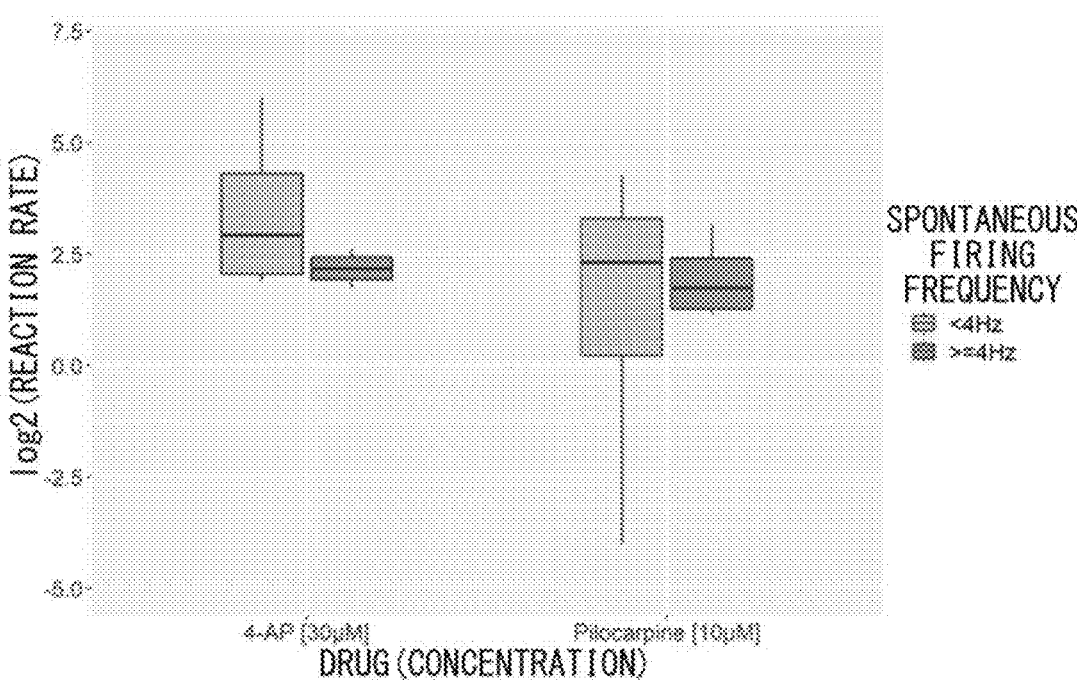
FIG. 5 is a graph showing the effect of exposure of 4-AP and Pilocarpine of this example to a cultured product on the firing frequency of the cultured product.

FIG. 5 shows the effect of exposure of 4-AP and Pilocarpine to the cultured product on the firing frequency of the cultured product. 4-AP was an exemplary inhibitor of ion channels related to neurotransmission, and Pilocarpine was used as an exemplary compound that competes with the binding of neurotransmitters to receptors related to neurotransmission. As shown in FIG. 5, when the spontaneous firing frequency of the cultured product before exposure to the test compound was 4 Hz or more for every 16 electrodes, the variation in the reaction rate of the firing frequency after exposure of the test compound was reduced as compared with when the spontaneous firing frequency was less than 4 Hz for every 16 electrodes (less than 0.25 Hz when the number of electrodes was 16).

Figure 10:
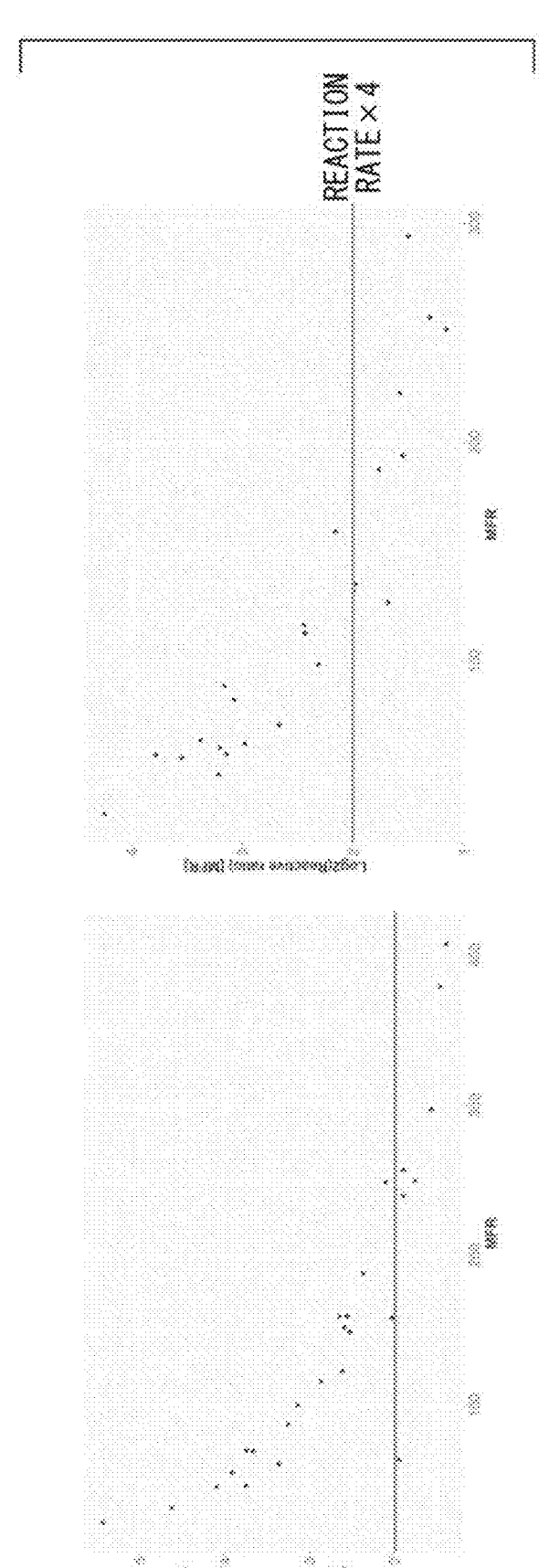
FIG. 10 is a graph a comparison of response rates between 4 and 400 Hz of spontaneous firing frequency of cultures prior to exposure to test compounds.

FIG. 10 shows a comparison of the spontaneous firing frequency of cultures prior to test compound exposure from 4 to 400 Hz per 16 electrodes. The left figure shows the data with 4-AP and the right figure show the data with Pilocarpine was used as the test compound, respectively. The line is shown at the point where the response rate is Log2 (response rate)=2, there is, the response rate to the test compound is 4 times. As shown in the figure, it is mainly 200 Hz or less, especially 100 Hz or less that shows a reaction rate of 4 times or more for each test compound. That is, when the spontaneous firing frequency of the culture before exposure to the test compound is 4 Hz or more and less than 100 Hz per 16 electrodes, both 4-AP and Pilocarpine show a response rate of 4 times or more, and respond well, while in 200 Hz or more, the response rate was only about half that. The above results indicate that this evaluation method can serve as a tool for screening and preparing highly effective pharmaceutical compositions.

Experimental Example 2

Using the plate produced in Experimental Example 1, a pharmacological test was performed using various drugs. The effect of the drug was confirmed by exposing an anti-epileptic drug having a function of inhibiting nerve firing to a sample. The evaluated drugs were Carbamazepine, Phenytoin, and Zonisamide, and the measurement was performed under the same conditions as the measurement of the extracellular potential data of Experimental Example 1.

Figure 6:
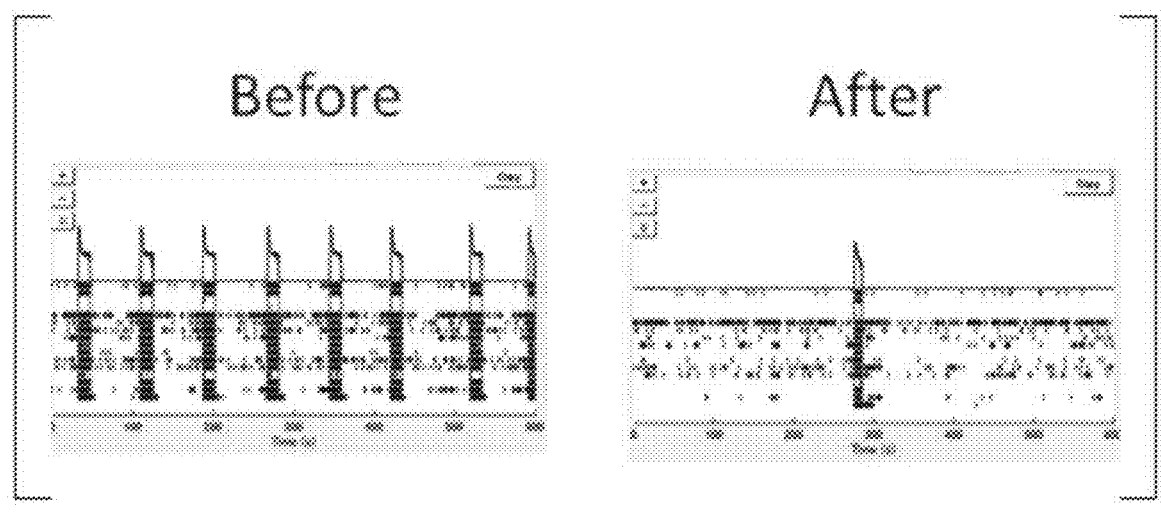
FIG. 6 is a graph showing a raster plot that visualizes the firing state of Carbamazepine of this example and the number of detected spikes.
Figure 7:
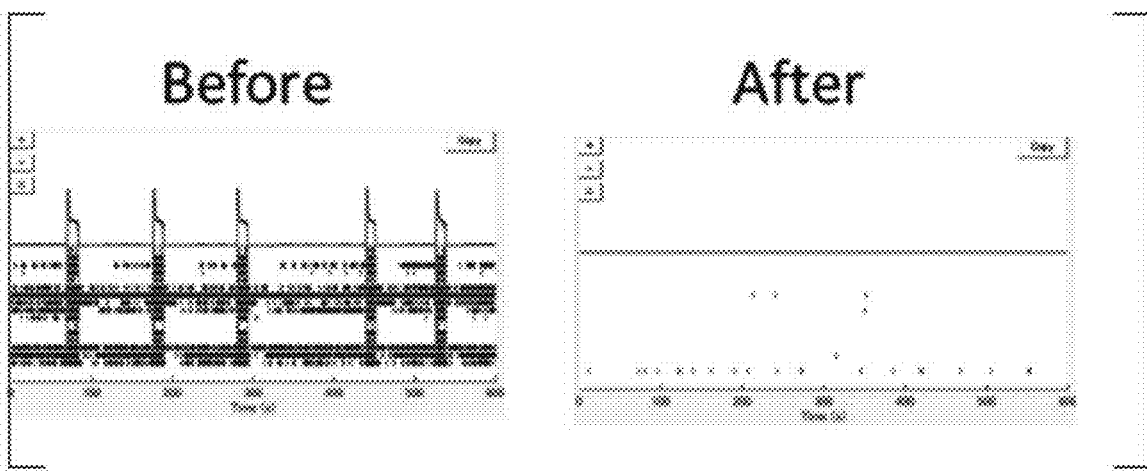
FIG. 7 is a graph showing a raster plot that visualizes the firing state of Phenytoin of this example and the number of detected spikes.
Figure 8:
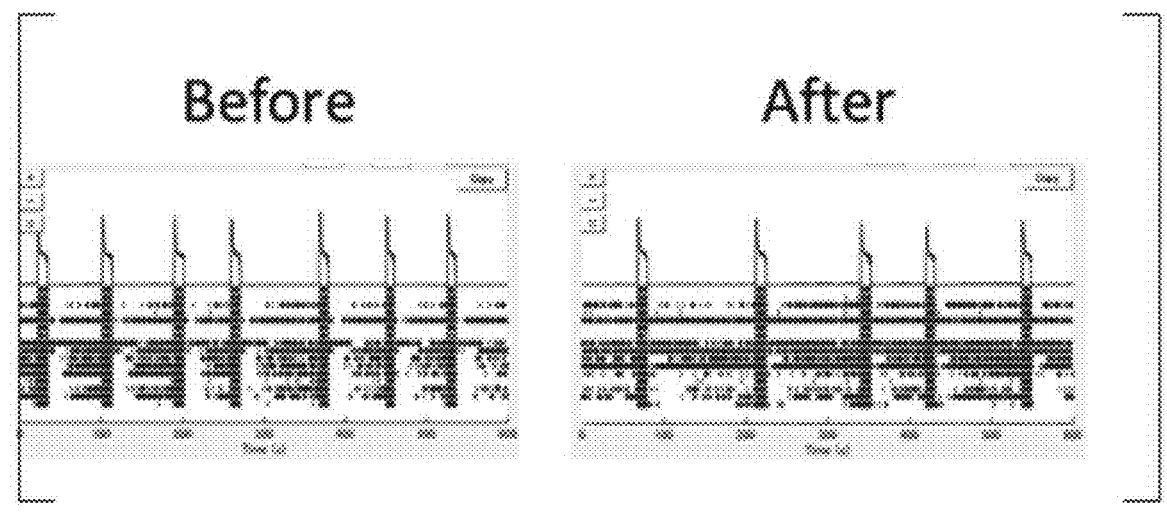
FIG. 8 is a graph showing a raster plot that visualizes the firing state of Zonisamide of this example and the number of detected spikes.

A graph of a raster plot that visualizes the firing state and the number of detected. spikes for each drug is shown for Carbamazepine in FIG. 6, Phenytoin in FIG. 7, and Zonisamide in FIG. 8. Before in the drawings indicates before drug exposure, and After indicates after drug exposure. In all of the drugs, it was observed that the spontaneous firing frequency that could be detected from the number of spikes after drug exposure was reduced, and the mode in which that firing activity of the nerve was reduced after drug exposure was confirmed. That is, it was observed that the plate of this example could be used for detection in the pharmacological test using various drugs.

The present invention includes the following aspects.

[1] A cell-containing structure for evaluating an electrical property of neurons, including:

(a) a culture surface to which the neurons are able to be adhered; (b) a cell mass that is adhered to the culture surface and contains at least one of the neurons; and (c) a plurality of electrodes for measuring the electrical property of the cell mass, wherein a spontaneous firing frequency of cells contained in the cell mass is 0.25 Hz or more per electrode.

[2] The cell-containing structure according to [1], wherein the neurons ns obtained by in vitro differentiation.

[3] The cell-containing structure according to [1] or [2], wherein the neurons are neurons derived from human induced pluripotent stem cells (hiPSC),

[4] The cell-containing structure according to [3], wherein the human induced pluripotent stem cells are derived from healthy people.

[5] The cell-containing structure according to [3], wherein the human induced pluripotent stem cells are derived from a human having a disease.

[6] The cell-containing structure according to [5], wherein the disease is a nervous disease.

[7] The cell-containing structure according to [6], wherein the nervous disease is autism, epilepsy, schizophrenia, ADHD, ALS or bipolar disorder.

[8] The cell-containing structure according to any one of [1] to [7], wherein the cell mass contains astrocytes.

[9] The cell-containing structure according to any one of [1] to [8], wherein the cell mass contains microglial cells or oligodendrocytes.

[10] The cell-containing structure according to any one of [1] to [9], further including a substrate which is an extracellular matrix.

[11] The cell-containing structure according to [10], wherein the extracellular matrix contains laminin.

[12] The cell-containing structure according to any one of [1] to [11], wherein the electrical property is detected by a response to at least one stimulus treatment applied to the cells or cell mass.

[13] The cell-containing structure according to [12], herein the stimulus treatment is exposure to at least one test compound.

[14] The cell-containing structure according to [13], wherein the test compound is an agonist or antagonist of a neurotransmitter receptor.

[15] The cell-containing structure according to [13], wherein the test compound is an ion channel blocker.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

1 Well bottom
2 Cultured product
3 Micro electrode
4 Plate
5 Well plate
6 Raster plot
7 Graph of number of spikes

PATENT DOCUMENT

[Patent Document 1] Japanese Patent No. 6761409

What is claimed is:

1. A method for preparing a cell-containing structure for evaluating an electrical property of neurons, comprising:
1) providing a cell containing structures comprising (a) a culture surface coated with a coating agent to which the neurons are able to be adhered;
(b) a cell mass that is adhered to the coated culture surface and contains the neurons; and
(c) a plurality of electrodes for measuring the electrical property of the cell mass,
2) determining a spontaneous firing frequency of cells contained in the cell mass and
3) retaining the cell-containing structures where the spontaneous firing frequency of cells contained in the cell mass is 0.25 Hz or more and less than 31.25 Hz, per electrode, thereby preparing a cell-containing structure for evaluating an electrical property of neurons.

2. The method according to claim 1,
wherein the neurons are neurons obtained by in vitro differentiation.

3. The method according to claim 1,
wherein the neurons are neurons derived from human artificial pluripotent stem cells (hiPSC).

4. The method according to claim 3,
wherein the human artificial pluripotent stem cells are derived from healthy people.

5. The method according to claim 3,
wherein the human artificial pluripotent stem cells are derived from a human having a disease.

6. The method according to claim 5,
wherein the disease is a nervous disease.

7. The method according to claim 5,
wherein the disease is autism, epilepsy, schizophrenia, ADHD, ALS or bipolar disorder.

8. The method according to claim 1,
wherein the cell mass contains astrocytes.

9. The method according to claim 1,
wherein the cell mass contains microglial cells or oligodendrocytes.

10. The method according to claim 1, further comprising a substrate which is an extracellular matrix.

11. The method according to claim 10,
wherein the extracellular matrix contains laminin.

12. The method according to claim 1,
wherein the electrical property is detected by a response to at least one stimulus treatment applied to the cell mass.

13. The method according to claim 12,
wherein the stimulus treatment is exposure to at least one test compound.

14. The method according to claim 13,
wherein the test compound is an agonist or antagonist of a neurotransmitter receptor.

15. The method according to claim 13,
wherein the test compound is an ion channel blocker.

* * * * *